(12) United States Patent  
Goddard et al.

(10) Patent No.: US 8,979,919 B2  
(45) Date of Patent: Mar. 17, 2015

(54) SYSTEM AND METHOD FOR POSITIONING A STENT GRAFT

(75) Inventors: Robert William Goddard, Didcot (GB); Duncan Keeble, Didcot (GB)

(73) Assignee: Anson Medical Limited (GB)

( * ) Notice: Subject to any disclaimer, the term of this patent is extended or adjusted under 35 U.S.C. 154(b) by 1210 days.

(21) Appl. No.: 12/445,344

(22) PCT Filed: Oct. 15, 2007

(86) PCT No.: PCT/GB2007/003922  
§ 371 (c)(1),  
(2), (4) Date: Aug. 24, 2010

(87) PCT Pub. No.: WO2008/047092  
PCT Pub. Date: Apr. 24, 2008

(65) Prior Publication Data  
US 2011/0125252 A1      May 26, 2011

(30) Foreign Application Priority Data  
Oct. 16, 2006   (GB) .................................. 0620495.2

(51) Int. Cl.  
*A61F 2/06*   (2013.01)  
*A61F 2/95*   (2013.01)

(52) U.S. Cl.  
CPC ........... *A61F 2/95* (2013.01); *A61F 2002/9511* (2013.01)  
USPC ....................................... 623/1.23; 623/1.11

(58) Field of Classification Search  
CPC ... A61F 2/95; A61F 2/954; A61F 2002/9511; A61F 2002/9534; A61F 2002/9505  
USPC ....................................... 623/1.23, 1.11, 2.11  
See application file for complete search history.

(56) References Cited

U.S. PATENT DOCUMENTS

| | | | | |
|---|---|---|---|---|
| 4,913,141 A * | 4/1990 | Hillstead | ....................... | 623/1.11 |
| 5,290,305 A   | 3/1994 | Inoue | | |
| 5,464,449 A * | 11/1995 | Ryan et al. | ................... | 623/1.23 |
| 5,531,785 A * | 7/1996 | Love et al. | ................... | 623/2.11 |
| 5,713,948 A * | 2/1998 | Uflacker | ....................... | 623/1.23 |
| 5,824,055 A * | 10/1998 | Spiridigliozzi et al. | ...... | 623/1.11 |
| 6,015,422 A * | 1/2000 | Kerr | ............................... | 606/191 |
| 6,099,548 A   | 8/2000 | Taheri | | |
| 6,102,918 A * | 8/2000 | Kerr | ............................... | 606/108 |
| 6,346,118 B1* | 2/2002 | Baker et al. | .................. | 623/1.12 |
| 6,471,722 B1* | 10/2002 | Inoue | ........................... | 623/1.35 |
| 6,723,116 B2* | 4/2004 | Taheri | .......................... | 623/1.11 |

(Continued)

FOREIGN PATENT DOCUMENTS

| | | |
|---|---|---|
| WO | WO 96/39104 A1 | 12/1996 |
| WO | WO 99/37242 A1 | 7/1999 |
| WO | WO 2004/017868 A1 | 3/2004 |

*Primary Examiner* — Gregory Anderson  
*Assistant Examiner* — Christopher L Templeton  
(74) *Attorney, Agent, or Firm* — Craig A. Fieschko, Esq.; DeWitt Ross & Stevens S.C.

(57) ABSTRACT

A stent graft can be held in place on the outside of the thoracic arch by a hypodermic needle tube which passes through a bore of the stent graft and back to the user. A center tube tethered to the stent graft at an end distal to the user is employed to hold the stent graft within the pulsatile blood flow, preventing the stent graft from collapsing during deployment. The position of both the hypodermic needle tube and the center tube can be controlled by the user by a control handle.

19 Claims, 5 Drawing Sheets

(56) References Cited

U.S. PATENT DOCUMENTS

| | | | |
|---|---|---|---|
| 6,821,291 B2 * | 11/2004 | Bolea et al. | 623/1.11 |
| 6,855,159 B1 * | 2/2005 | Tanner et al. | 623/1.11 |
| 6,878,159 B2 * | 4/2005 | Iwasaka et al. | 623/1.11 |
| 6,899,728 B1 | 5/2005 | Phillips et al. | |
| 7,611,528 B2 * | 11/2009 | Goodson et al. | 623/1.11 |
| 7,758,626 B2 * | 7/2010 | Kim et al. | 623/1.11 |
| 7,854,758 B2 * | 12/2010 | Taheri | 623/1.23 |
| 7,942,921 B2 * | 5/2011 | Nissl et al. | 623/1.15 |
| 7,993,383 B2 * | 8/2011 | Hartley et al. | 623/1.11 |
| 2002/0091439 A1 | 7/2002 | Baker et al. | |
| 2002/0151953 A1 * | 10/2002 | Chobotov et al. | 623/1.11 |
| 2002/0173837 A1 * | 11/2002 | Lauterjung | 623/1.12 |
| 2003/0050684 A1 * | 3/2003 | Abrams et al. | 623/1.11 |
| 2003/0195607 A1 | 10/2003 | Trout, III et al. | |
| 2004/0243215 A1 | 12/2004 | Nelson | |
| 2005/0143806 A1 | 6/2005 | Phillips | |
| 2006/0004433 A1 | 1/2006 | Greenberg et al. | |
| 2006/0155358 A1 | 7/2006 | LaDuca et al. | |

\* cited by examiner

SYSTEM AND METHOD FOR POSITIONING A STENT GRAFT

FIELD OF THE INVENTION

The present application relates to apparatus and a method for positioning a stent graft in vivo. In particular, it relates to the positioning of a stent graft in the arch of the thoracic aorta.

BACKGROUND OF THE INVENTION

An endovascular stent graft is designed to exclude the flow of blood to an aneurysm that has been formed within the wall of the aorta. This is achieved by accessing the aneurysm via an artery, usually within the patient's leg, with a system designed to deliver, position and deploy the stent graft so that it bridges and seals off the aneurysm.

A stent graft is a tubular device with walls made from a flexible sheet material, supported by a rigidising frame which is usually formed from super-elastic metal. Some stent graft designs are fixed to the aorta wall by means of barbs or hooks. The rigidising frame maintains the tubular shape of the stent graft, while providing a radial sealing force to create a proximal and distal seal with the aortic wall.

In the thoracic aorta it is becoming increasingly desirable to place the proximal end of the stent graft within the arch of the aorta, sometimes as proximal as between the brachiocephalic artery and the left carotid artery. In some applications, such as the placement of percutaneous heart valves, it is envisaged that the stent graft should be placed at the very origin of the aorta.

Placement of stent grafts in the arch of the aorta is particularly difficult because of the force of blood ejected from the heart. In more distal vessels, the capacity of the aorta between the heart and the landing zone of the device is significant and reduces the maximum velocity of blood experienced by the graft. In the arch of the aorta, the capacity of the vessel between the heart and the landing zone of the stent graft is minimal and hence the stent graft is subject to the full ejection velocity of blood from the heart.

The effect of this force with current devices is usually to turn the proximal end of the device to lift it away from the wall of the aorta, commonly at the inner wall of the arch. Over time, the extent of this turn can increase, reducing the flow of blood in the distal aorta and potential leading to failure of the fixation system of the stent graft. In order to overcome this problem the delivery system employed to place the stent graft must be capable of controlling the angle of the proximal end of the stent graft in the vessel wall.

SUMMARY OF THE INVENTION

In accordance with a first aspect of the present invention, there is provided a system for positioning a stent graft in vivo comprising a tubular stent graft having first and second ends at either end of a bore, a first positioner releasably attached to the stent graft closer to the first than to the second end, a second positioner releasably attached to the stent graft closer to the first than to the second end, means for controlling the position of the first and second positioners, a first connector connecting the first positioner to said means for controlling, and a second connector connecting the second positioner to said means for controlling, the first and second connectors passing from the first and second positioners through the bore of the stent graft and exiting the bore closer to the second than the first end of the stent graft, characterized in that the system comprises a flexible link releasably attaching at least one of the first and second positioners to the stent graft.

In accordance with a second aspect of the present invention there is provided a system for positioning a stent graft in vivo comprising a tubular stent graft having first and second ends at either end of a bore, a first positioner releasably attached to the stent graft closer to the first than to the second end, a second positioner releasably attached to the stent graft closer to the first than to the second end, means for controlling the position of the first and second positioners, a first connector connecting the first positioner to said means for controlling, and a second connector connecting the second positioner to said means for controlling, the first and second connectors passing from the first and second positioners through the bore of the stent graft and exiting the bore closer to the second than the first end of the stent graft, characterized in that the means for controlling the position of the first and second positioners is operable to control said positions independently. Preferable, this system additionally comprises a flexible link releasably attaching at least one of the first and second positioners to the stent graft.

"Position" as used herein means to hold in a fixed position as well as to move into position.

"Flexible" as used herein means sufficiently flexible to be flexed around the curves of the body lumen without breaking.

The terms "proximal" and "distal" with regard to the stent graft are used here with the following industry-accepted meaning—that "proximal" means the end of the graft nearer to the heart and "distal" means the end of the graft furthest from the heart when the stent graft is in vivo.

The first and second connectors preferably comprise first and second elongate elements and the ends of the elongate elements distal to the means for controlling form the first and second positioners. Thus in a preferred embodiment the elongate elements are connected at one end to the control handle of the system and are releasably attached at the other end to the mouth of the stent graft distal to the control handle.

There are a number of prior art references which disclose various types of elongate elements for remotely controlling deployment of a stent graft. However, none of these are concerned with the same type of control as in the present invention, and as a result are structurally different from the system of the present invention.

WO 2004/017868 (William A. Cook Australia Pty. Ltd.) discloses an arrangement for mounting a stent graft prosthesis onto a deployment device. WO 96/39104 (Orth) discloses apparatus for deploying a graft. However, both of these references are concerned with controlling deployment of expandable stent grafts. They both disclose single elongate elements attached in a plurality of places to the stent graft.

US 2004/0243215 (Nelson) discloses a system for staged expansion of an endograft which comprises restraining members on the outside of the graft.

US 2006/0004433 (Cook Incorporated) is also concerned with staged expansion of a stent graft rather than positioning the mouth of the stent graft during deployment.

In accordance with a third aspect of the invention, there is provided method for positioning a stent graft in vivo comprising the steps of:
(a) providing a system as defined above;
(b) moving the stent graft until it is proximate the intended final position;
(c) controlling the first positioner to position the part of the stent graft to which it is attached;
(d) controlling the second positioner to position the part of the stent graft to which it is attached;

(e) detaching the first positioner from the stent graft; and
(f) detaching the second positioner from the stent graft.

Preferably the first and second positioners are controlled independently.

The preferred embodiment is a system of wires and tethers which allow the inclination of the proximal part of the graft to the axis of the aorta to be, controlled from the handle of the delivery system which places the stent graft into the patient. Specifically, the proximal end of the stent graft can be considered to define a plane and this plane should lie substantially perpendicular to the longitudinal axis of the aorta at that point. The control system described below allows the said plane to be inclined to the axis of the vessel under the control of the user. Angles of inclination from −45° to +45° can be achieved with the system although practical clinical use is likely to be limited to angles of −10° to +10°.

In order to incline the end of the stent graft to the axis of the artery at least one turning couple must be applied to the end. In practice, this turning couple can be achieved by a variety of paired mechanisms capable of differential movement. A first part of the pair must at least be capable of holding a section of the mouth of the stent graft at a constant distance from the handle of the delivery system while the second part is capable of movement relative to the first part and is preferably connected to an opposed part of the mouth of the stent graft. For more complete control, one part of the pair should provide a method of moving part of the stent graft away from the handle of the delivery system while the other part of the pair should provide a method of moving an opposed part of the stent graft towards the handle.

Dependent upon the detailed characteristics of the stent graft, half the couple referred to above can be provided by the wall of the stent graft if it has sufficient columnar stiffness. In this instance, the second half of the couple can be provided by a single elongate element whose first end is attached to a control mechanism in the handle and whose second end is releasably connected to the mouth of the stent graft. Tension applied to the elongate element will be applied to the mouth of the stent graft at the point of attachment of the elongate element and will move that part of the mouth towards the handle of the delivery system. The stiffness of the implant will provide the maximum turning couple at a point on the mouth of the stent graft opposite the attachment point of the elongate element, causing the mouth of the stent graft to turn towards the elongate element.

The elongate element and the means for attaching it to the stent graft are preferably attached to a control knob in the handle of the delivery system which itself has two functions:
1) The ability to move or to hold in position the elongate element in the vessel (The Position Control);
2) The ability to release the attachment means so as to disconnect the elongate element from the stent graft (The Release Control).

The releasable attachment means may simply be a length of thread whose first end is connected to the Position Control and which is extended through the delivery system to the mouth of the stent graft, threaded through the wall of the stent graft and then returned through the delivery system back to the handle where it is connected to the Release Control. Axial movement of the Position Control will have the effect of lengthening or shortening the thread, moving the attached part of the mouth closer or further away from the handle. Operation of the Release Control to free one end of the thread will allow the Position Control to be used to pull the thread through the wall of the stent graft, allowing it to be released.

Such an arrangement is difficult to operate reliably in clinical circumstances because a considerable length of thread must be pulled through the stent graft and the thread can snag or catch on itself or other structures, trapping it and attached structures in the patient.

For this reason a preferred arrangement includes a separate release wire or fibre which is used to disconnect the elongate element at its point of connection with the stent graft, removing the risk of pulling long structures.

The elongate element may be formed from a thread, fibre or wire which has at least one hole or loop formed at its end. It is attached to the mouth of the stent graft by threading the release fibre through the wall of the graft and the loop or hole formed at the end of the elongate element. Pulling the release fibre disrupts the attachment of the elongate element to the wall of the stent graft. Such an arrangement can provide tension to the point of connection but cannot provide a compressive force.

The above construction of elongate element is flexible and may conveniently be used either to pull the implant directly towards the handle of the delivery system or, by means of a turning point on the delivery system placed beyond the mouth of the stent graft, it can be used to pull the implant away from the handle of the delivery system. Two of these flexible elongate elements can be arranged to operate in opposition at the same point of attachment to provide a more complex, but more complete control of the point of attachment.

The elongate element can be arranged to be more rigid by forming it from harder materials or building it from heavier gauge materials.

In the interests of simplicity, a single couple is adequate, particularly in the thoracic aorta; however, more than one couple can be used to control the inclination of the mouth of the graft in three dimensions or to control the shape of the mouth of the graft, if the graft is of a suitably deformable construction.

Conveniently, one elongate element can be provided by a length of hypodermic needle tube with a first end connected to the mouth of the stent graft, said tube running from the stent graft until its second end is joined to a control knob on the handle of the delivery system. The wall of the said tube is preferably perforated in two places close to the first end of the tube. A wire or fibre for attaching the hypodermic tube to the stent graft is drawn through the tube from the second end to emerge from the first perforation. The wire or fibre is then passed through the part of the stent graft to be controlled, which is typically a point on the edge of the mouth at the proximal end of the device. The wire or fibre is then passed through the second perforation of the said tube and is continued along the lumen of the tube until an adequate degree of fixation of the stent graft to the tube has been achieved.

A number of materials and dimensions can be employed for the elongate element. A functional solution can be made with hypodermic tube with an internal diameter of 0.3 mm and an external diameter of 0.5 mm, with a hard drawn stainless steel wire of 0.2 mm diameter passing through the lumen of the tube. With such a system, it is advantageous to form a curve in the hypodermic tube between the first and second perforations so that the path taken by the stainless wire is not too tortuous.

Prototypes of the elongate element have been constructed employing PEEK tube and monofilament nylon (and also monofilament PEEK) but this system has not been tested clinically.

An important feature of the elongate element is that it can be released from the stent graft when the user so wishes. The release of the elongate element described above can be effected by pulling the central wire or fibre from the second end of the hypodermic tube so that the further end of the wire or fibre is pulled out of the second perforation, through the wall of the stent graft and through the first perforation. It is convenient if the central wire or fibre is attached to another control knob on the handle of the delivery system.

The second elongate element can be constructed in the same manner as the first. Two of the above described structures can be used to provide the turning couple needed to control orientation of the mouth of the device.

Preferably however, the second elongate element involves a thinner and more flexible construction than the first and is constructed from a fibre or thread which is attached to a part of the stent graft opposite the attachment point of the first elongate element. The thread is then run in the direction in which control is required. For instance, the thread can be run directly back to a control knob on the handle to pull the part of the stent graft where the pulling means is attached distally. Alternatively, the second elongate element can be run further into the patient, turned around a turning point on the delivery system, and then run back to the handle. This latter arrangement will pull the connected part of the stent graft proximally.

The second elongate element can be released from the stent graft by using a double length of fibre or thread which is looped through the stent graft. Tension is applied to the stent graft by pulling both ends of the fibre or thread together; the fibre or thread can be released by pulling on only one end and drawing the complete length of fibre or thread out of the stent graft.

An improved method of releasing the pulling fibre or thread is to weave the thread through the structure of the stent graft and to lock it in place by a second fibre, wire or thread. For example, a loop may be formed in the pulling thread and the second fibre, wire or thread passed through this loop and then threaded through the wall of the stent graft to attach the pulling thread thereto. On pulling this second fibre, wire or thread, the first fibre or thread can be pulled free of the stent graft.

By combining one elongate element of each construction, the stent graft delivery system has the benefit of high positional control from the first elongate element and flexibility and small size from the second elongate element.

Moreover, experience has shown that the most advantageous arrangement of the first elongate element is to orientate it on the outside of the curve of the thoracic arch. All branch vessels originate from this side of the thoracic arch and in order to avoid accidentally placing the stent graft over one of these vessels, the greatest control is needed of the delivery system in this region.

It follows that the second elongate element is preferably opposite the first and the preferred location for the second elongate element is on the inside of the curve of the thoracic arch. It has been found experimentally with the Lombard Aorfix stent graft (disclosed in WO 99/37242, the contents of which are incorporated herein by reference) that the second elongate element is most effective when pulling the connected part of the stent graft proximally rather than distally. It may be found that in the case of other stent graft designs different combinations are preferable.

In accordance with a further aspect of the invention, there is provided apparatus for positioning a stent graft in vivo comprising a first elongate element and means for attaching the first elongate element to the stent graft and a second elongate element and means for attaching the second elongate element to the stent graft, wherein the first and second elongate elements are independently controllable.

BRIEF DESCRIPTION OF THE DRAWINGS

A number of preferred embodiments of the invention will now be described with reference to the drawings, in which:—

DETAILED DESCRIPTION OF PREFERRED EMBODIMENTS OF THE INVENTION

Figure 1A:
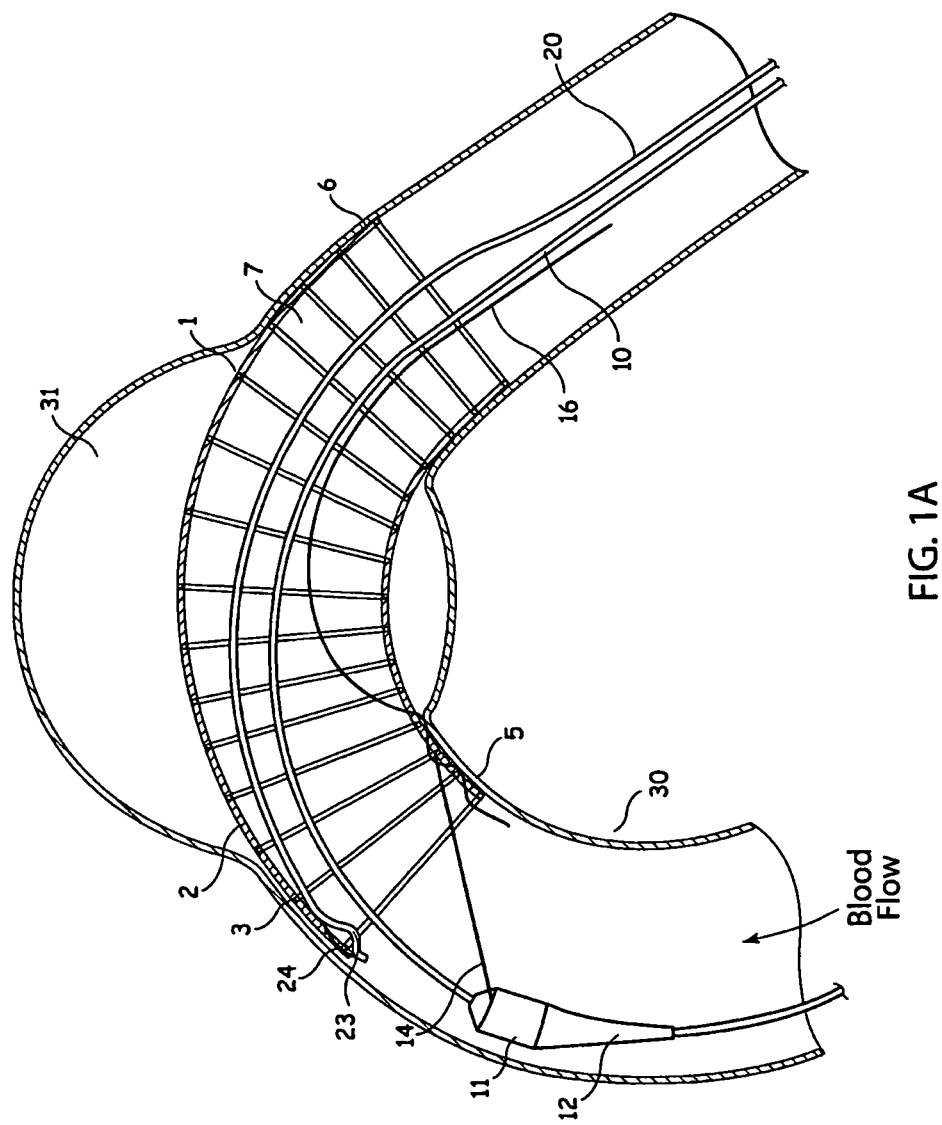
FIG. 1A shows a cross-section of a stent graft correctly positioned at the thoracic arch prior to release.
Figure 1B:
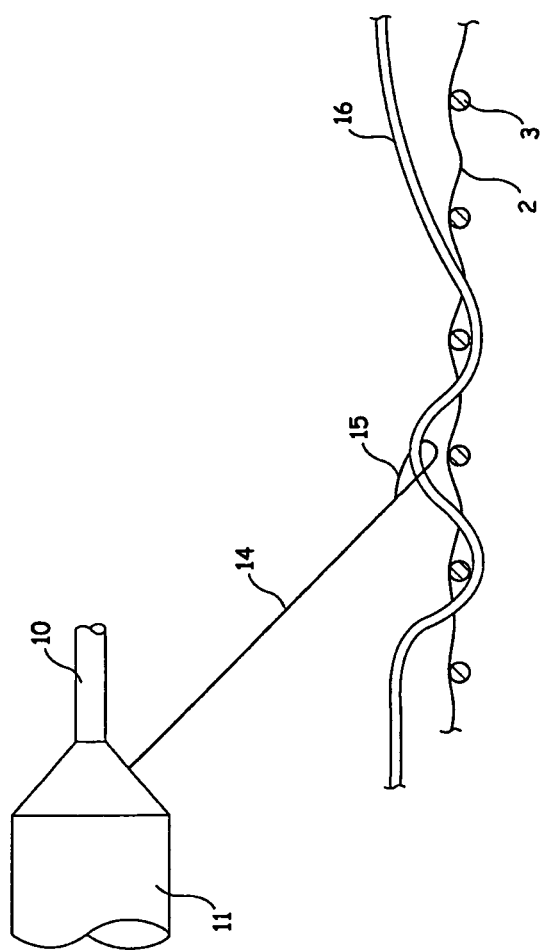
FIG. 1B shows an enlarged view of the connection between the centre tube and the stent graft of FIG. 1A.
Figure 1C:
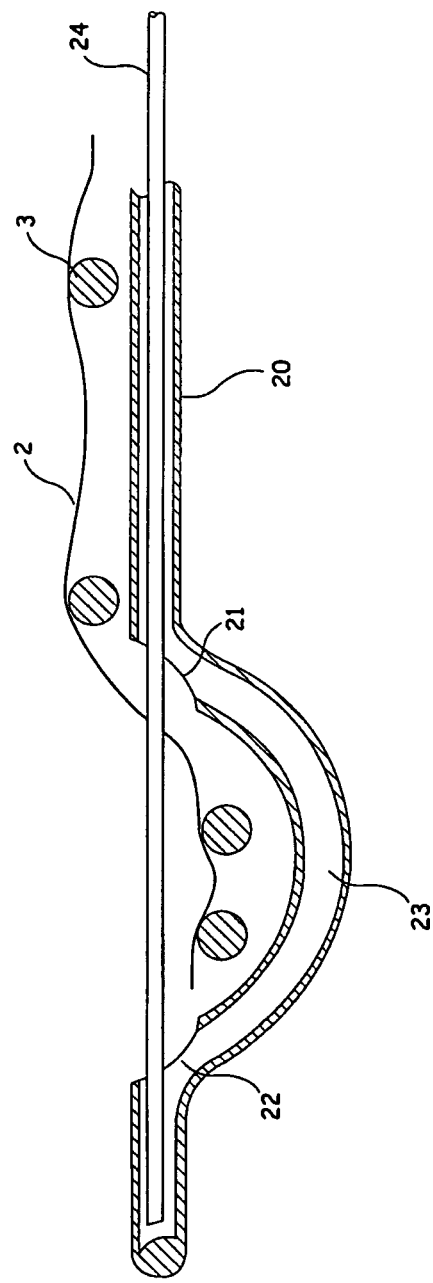
FIG. 1C shows an enlarged view of the connection between the hypodermic needle tube and the stent graft of FIG. 1A.

Turning to FIGS. 1A, 1B and 1C, stent graft 1 comprises graft material 2 and stent material 3 in the form of hoops of reinforcement wire encircling stent graft 1. Graft material 2 and stent material 3 are in the form of a tube having proximal end 5 and distal end 6 at either end of bore 7.

Figure 3:
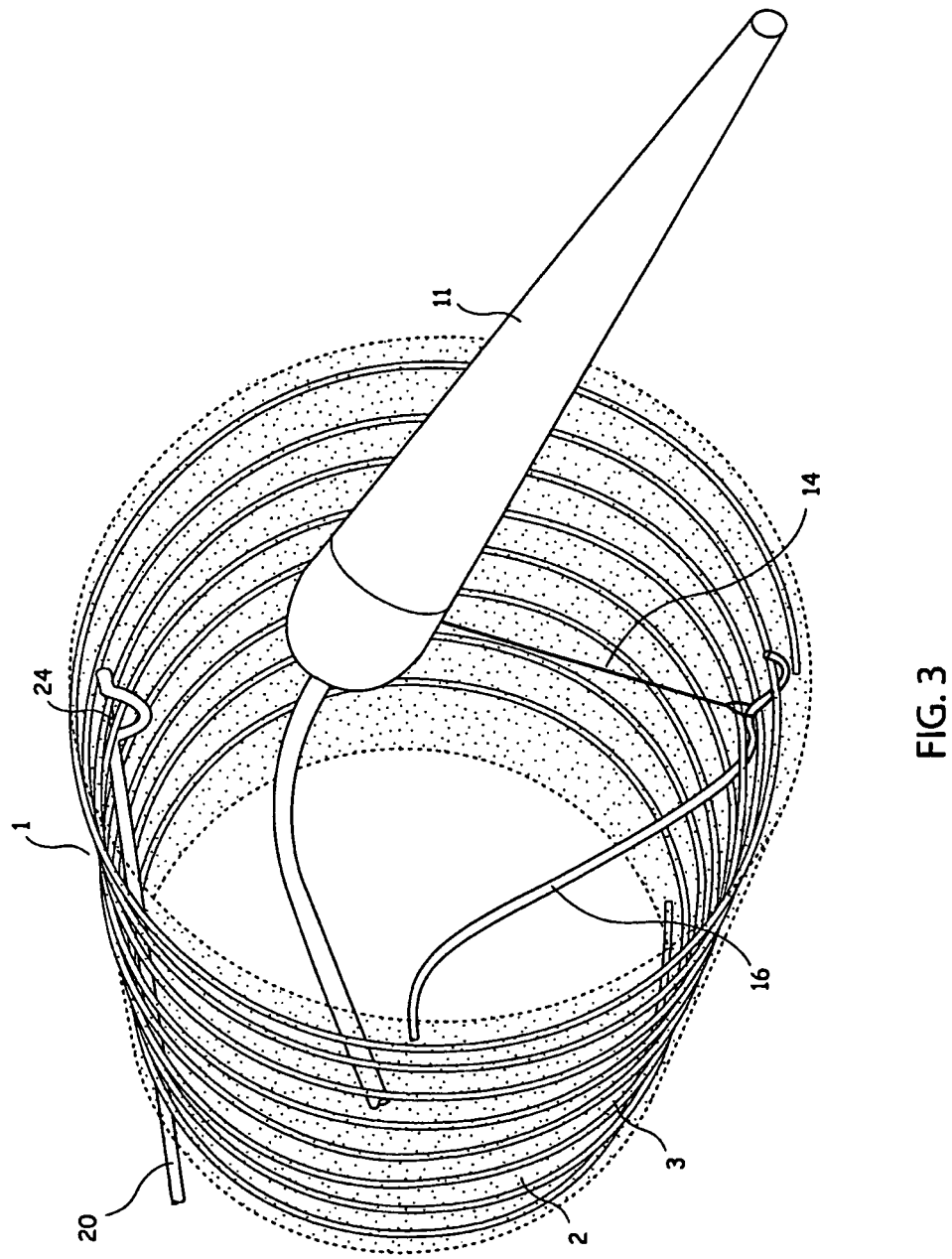
FIG. 3 is a schematic depiction of the stent graft held of the present invention held in place at the thoracic arch (not shown).

FIG. 1A shows deployed stent graft 1 held in position at thoracic aorta aneurysm 31 at the curve of the thoracic arch 30 by apparatus in accordance with the invention. A schematic drawing of this arrangement is shown in FIG. 3.

As can be seen from FIGS. 1A and 1C, stent graft 1 is held in place on the outside of the thoracic arch by hypodermic needle tube 20 which passes through bore 7 of stent graft 1 and back to the user. In use, the end of the hypodermic tube distal to the user curves from a straight configuration into arch 23 with two apertures 21, 22 at the base of the arch. Fixer wire 24 is housed in the bore of hypodermic tube 20, and wire 24 exits tube 20 from the aperture 21 proximate the user and re-enters the tube 20 through the second aperture 22 after passing through the wall of graft 1, thus attaching the hypodermic tube 20 to the graft 1.

As can be seen from FIGS. 1A and 1B, centre tube 10 has tip 11 and nosecone 12 at the end distal to the user which passes through bore 7 of stent graft 1 and back to the user. Tether 14 connects tip 11 of centre tube 10 to a part of the stent graft at the inside of thoracic arch 30. Tether 14 is either attached to tip 11 or (preferably) passes through an aperture (not shown) in tip 11 and is returned back to the user by some convenient means. As can be seen from FIG. 1B, tether release fibre 16 is threaded through the wall of stent graft 1 and then passes through loop 15 at the end of tether 14 and thereby attaches tether 14 to stent graft 1. Tether release fibre 16 then passes down bore 7 of stent graft 1 and back to the user.

During deployment of stent graft 1, tether 14 is put under tension and, supported by tip 11 and centre tube 10, holds stent graft 1 within the pulsatile blood flow preventing stent graft 1 from collapsing.

Following deployment, the delivery system has to be detached from the deployed stent graft. This is achieved by disconnecting the two attachment points, which are tether 14 and hypodermic tube 20 positioned on the outer thoracic arch 30. It will be appreciated that this is firstly simply a matter of the user pulling on the proximate end of fixer wire 24 so that that distal end disengages from the wall of stent graft 1 and retracts inside hypodermic tube 20. Similarly, tether 14 is detached from stent graft 1 by simply pulling on the end of tether release fibre 16 proximate the user to unthread it from the wall of stent graft 1 and from loop 15 at the end of tether 14. The attachment points can either be released simultaneously or hypodermic tube 20 can be released shortly before releasing tether 14.

Finally, centre tube 10, hypodermic tube 20, tether 14 and tether release fibre 16 can all be retracted by the user to leave stent graft 1 in place in vivo.

Figure 2:
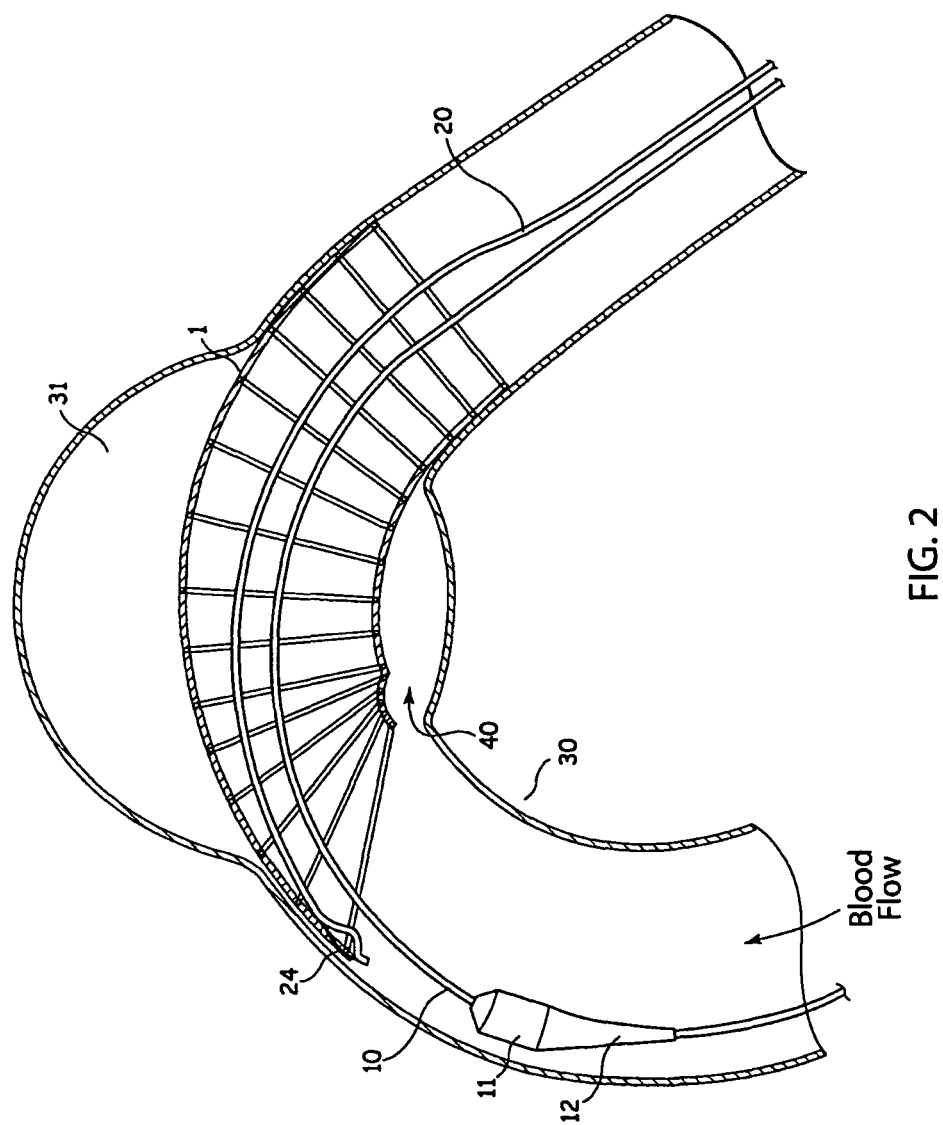
FIG. 2 shows for comparison a stent graft positioned at the thoracic arch without employing the entire apparatus of the present invention.

FIG. 2 shows stent graft 1 which has been positioned at thoracic arch 30 with the use of hypodermic needle tube 20 but without employing the tether arrangement described above. As can be seen, the blood flow from the heart applies sufficient pressure to stent graft 1 at the inner arch that it lifts away from the artery wall and allows blood to leak 40 into the thoracic aneurysm 31, resulting in potential failure of stent graft 1.

The invention claimed is:

1. A system for positioning a stent graft in vivo comprising:
   a. a tubular stent graft having first and second graft ends at opposing ends of a graft bore,
   b. first and second positioners, each positioner:
      (1) being releasably attached to the stent graft closer to the first graft end than to the second graft end, and
      (2) including a positioner connection:
         (a) extending through the graft bore, and
         (b) exiting the graft bore closer to the second graft end than the first graft end,
   wherein:
   A. at least one of the positioners is repositionable with respect to the other along the axial length of the graft bore via the positioner's positioner connection,
   B. one of the first and second positioners:
      I. extends beyond the first graft end further than the other of the positioners with respect to the first graft end,
      II. is configured to pull the stent graft in one direction, and
      III. defines a turning point at its attachment to the stent graft,
   C. the other of the positioners is configured to pull the stent graft in an opposing direction, thereby providing a turning couple whereby the first graft end can be rotated about the turning point,
   D. at least one of the positioner connections includes a flexible tube,
   E. a flexible element is movably situated within the tube, and
   F. the tube includes a wall having an aperture through which the flexible element passes to releasably attach to the stent graft.

2. The system of claim 1 wherein each positioner and its positioner connection together define an elongated element.

3. The system of claim 1 wherein the tube wall includes two apertures therein, with the flexible element exiting the tube through one aperture and entering the tube through the other aperture.

4. The system of claim 1 wherein the first and second positioners are releasably attached to the stent graft at locations which are at least substantially diametrically opposite each other about the circumference of the stent graft.

5. The system of claim 1 wherein at least one of the first and second positioner is releasably attached to the stent graft by a second positioner flexible element perforating a wall of the stent graft.

6. The system of claim 5 wherein a flexible link extends between the second positioner flexible element and one of the positioners.

7. The system of claim 6 wherein:
   a. the flexible link bears a loop; and
   b. the second positioner flexible element extends through the loop of the flexible link.

8. The system of claim 7 wherein the flexible link is at least substantially formed from a thread.

9. A system for positioning a stent graft in vivo comprising:
   a. a tubular stent graft having first and second graft ends at opposing ends of a graft bore,
   b. first and second positioners, each positioner:
      (1) being releasably attached to the stent graft closer to the first graft end than to the second graft end, and
      (2) including a positioner connection:
         (a) extending through the graft bore, and
         (b) exiting the graft bore closer to the second graft end than the first graft end,
   c. a flexible element which perforates a wall of the stent graft,
   wherein:
   A. at least one of the positioners is repositionable with respect to the other along the axial length of the graft bore via the positioner's positioner connection,
   B. at least one of the positioners:
      I. extends beyond the first graft end further than the other of the positioners with respect to the first graft end, and
      II. is releasably attached to the stent graft by a thread extending between the positioner and the stent graft,
   C. the thread has an end bearing a loop,
   D. the flexible element passes through the loop.

10. A system for positioning a stent graft in vivo comprising:
    a. a tubular stent graft having first and second graft ends at either end of a graft bore,
    b. a first positioner extending forwardly from the second graft end along the interior of the graft bore, the first positioner including:
       (1) a flexible tube,
       (2) a flexible element extending within the flexible tube, wherein the flexible element protrudes from the tube to releasably attach to a first portion of the stent graft closer to the first graft end than to the second graft end;
    c. a second positioner extending forwardly from the second graft end along the interior of the graft bore and:
       (1) past the first graft end, and
       (2) further than the first positioner with respect to the first graft end,
       the second positioner including a flexible link extending rearwardly therefrom and being releasably attached to a second portion of the stent graft closer to the first graft end than to the second graft end, with the second positioner and second portion of the stent graft being spaced apart with the flexible link extending therebetween;
    wherein the second portion of the stent graft is situated at least substantially opposite the first portion of the stent graft about the circumference of the stent graft.

11. The system of claim 10 wherein:
    a. the flexible link bears a loop,
    b. the second positioner further includes a second positioner flexible element piercing a wall of the stent graft, second positioner the flexible element extending through the loop of the flexible link.

12. The system of claim 10 wherein the flexible link extends from a tip provided on the second positioner, wherein the tip tapers in diameter along its length.

13. A system for positioning a stent graft in vivo comprising:
    a. a tubular stent graft having first and second graft ends at either end of a graft bore, b. a first positioner extending from the second graft end along the interior of the graft bore, the first positioner including:
  (1) a flexible tube,
  (2) a first positioner flexible element extending within the flexible tube, wherein the first positioner flexible element protrudes from the tube to releasably attach to a first portion of the stent graft closer to the first graft end than to the second graft end;
c. a second positioner extending from the second graft end along the interior of the graft bore, the second positioner including:
  (1) a flexible link:
    (a) extending therefrom and being releasably attached to a second portion of the stent graft closer to the first graft end than to the second graft end,
    (b) bearing a loop,
  (2) a second positioner flexible element piercing a wall of the stent graft, the second positioner flexible element extending through the loop of the flexible link, wherein the second positioner flexible element extends from the second graft end along the interior of the graft bore to pierce the wall of the stent graft closer to the first graft end than to the second graft end,
wherein the second portion of the stent graft is situated at least substantially opposite the first portion of the stent graft about the circumference of the stent graft.

14. The system of claim 13 wherein the second positioner flexible element pierces the wall of the stent graft at least three times, with the loop of the flexible link being situated between at least two of the piercings.

15. A system for positioning a stent graft in vivo comprising:
a. a tubular stent graft having first and second graft ends at opposing ends of a graft bore,
b. first and second positioners, each positioner:
  (1) being releasably attached to the stent graft closer to the first graft end than to the second graft end, and
  (2) including a positioner connection:
    (a) extending through the graft bore, and
    (b) exiting the graft bore closer to the second graft end than the first graft end,
wherein:
A. at least one of the positioners is repositionable with respect to the other along the axial length of the graft bore via the positioner's positioner connection,
B. one of the first and second positioners:
  I. extends beyond the first graft end further than the other of the positioners with respect to the first graft end,
  II. is configured to pull the stent graft in one direction, and
  III. defines a turning point at its attachment to the stent graft,
C. the other of the positioners is configured to pull the stent graft in an opposing direction, thereby providing a turning couple whereby the first graft end can be rotated about the turning point,
D. at least one of the first and second positioner is releasably attached to the stent graft by a flexible element perforating a wall of the stent graft,
E. a flexible link extends between the flexible element and the positioner releasably attached to the stent graft by the flexible element.

16. The system of claim 15 wherein each positioner and its positioner connection together define an elongated element.

17. The system of claim 15 wherein:
a. the positioner other than the positioner releasably attached to the stent graft by the flexible element includes a tube flexible tube having the flexible element movably situated therein, and
b. the flexible tube includes a tube wall having two apertures therein, with the tube flexible element exiting the tube through one aperture and entering the tube through the other aperture.

18. The system of claim 15 wherein the first and second positioners are releasably attached to the stent graft at locations which are at least substantially diametrically opposite each other about the circumference of the stent graft.

19. The system of claim 15 wherein:
a. the flexible link bears a loop; and
b. the flexible element extends through the loop of the flexible link.

* * * * *